United States Patent [19]
Levin et al.

[11] Patent Number: 5,698,100
[45] Date of Patent: Dec. 16, 1997

[54] BACTERIOSTATIC DIALYZERS CONTAINING CITRIC ACID SOLUTIONS

[76] Inventors: Nathan Levin, 401 E. 34 St. - Apt. N30B, New York, N.Y. 10016; Hans-Dietrich Polaschegg, Grunwiesenweg 9, D 61440 Oberursel, Germany

[21] Appl. No.: 794,293

[22] Filed: Feb. 3, 1997

Related U.S. Application Data

[60] Continuation of Ser. No. 452,570, May 25, 1995, abandoned, which is a division of Ser. No. 134,098, Oct. 8, 1993, Pat. No. 5,480,565.

[51] Int. Cl.$^6$ .......................... B01D 65/02; B01D 65/06; A61L 2/16
[52] U.S. Cl. .................. 210/321.6; 210/321.72; 210/749; 210/764; 422/1; 422/28
[58] Field of Search .................. 210/321.6, 321.72, 210/646, 749, 764; 422/1, 26, 27, 28; 252/131

[56] References Cited

U.S. PATENT DOCUMENTS

| | | | |
|---|---|---|---|
| 4,199,469 | 4/1980 | Walzer | 134/24 |
| 4,411,866 | 10/1983 | Kanno | 422/25 |
| 4,647,458 | 3/1987 | Ueno et al. | 422/28 |
| 4,690,772 | 9/1987 | Tell et al. | 252/106 |
| 4,695,385 | 9/1987 | Boag | 210/764 |
| 5,173,125 | 12/1992 | Felding | 134/22.11 |
| 5,192,459 | 3/1993 | Tell et al. | 252/106 |
| 5,304,349 | 4/1994 | Polaschegg | 422/101 |

FOREIGN PATENT DOCUMENTS

| | | |
|---|---|---|
| 393386 | 10/1990 | European Pat. Off. |
| 505763 | 9/1992 | European Pat. Off. |

OTHER PUBLICATIONS

Deane et al., "Multiple Use of Hemodialyzers," In: *Replacement of Renal Function by Dialysis*, 3rd edition, edited by JF Maher, Kluwer Academic Publishers, Boston, Massachusetts, 1989, pp. 400–416.

*Reuse of Hemodialyzers—AAMI Recommended Practice for Reprocessing Hemodialyzers*, ANSI/AAMI RD47, Association for the Advancement of Medical Instrumentation, Arlington, Virginia, 1993, pp. i–vii and 1–25.

Kaufman et al., "Clinical Experience with Heat Sterilization for Reprocessing Dialyzers," *ASAIO Transactions*, vol. 38, No. 3, Jul.–Sep. 1992, pp. M338–M340.

*Primary Examiner*—John Kim
*Attorney, Agent, or Firm*—Maurice M. Klee

[57] ABSTRACT

A method for reprocessing dialyzer cartridges used with kidney dialysis machines is provided. The method involves filling the blood and dialysate compartments of the dialyzer with an aqueous solution containing citric acid at a concentration of 1.0–5.0 wt. %, e.g., 1.5 wt. %, and then subjecting the dialyzer to an elevated temperature above 90° C. and below 100° C., e.g., 95° C., for a period of at least 15 hours, e.g., 20 hours. Although citric acid is non-toxic and the temperature used is below the boiling point of water, the process has been found to produce a fully sterilized dialyzer. After reprocessing, the aqueous citric acid solution is preferably left in the dialyzer where it acts as a bacteriostatic agent during storage. Essentially no damage to the dialyzer and, in particular, to its semipermeable membrane results from either the reprocessing or storage procedures.

4 Claims, 2 Drawing Sheets

BACTERIOSTATIC DIALYZERS CONTAINING CITRIC ACID SOLUTIONS

This application is a continuation application of application Ser. No. 08/452,570 filed on May 25, 1995, now abandoned, which is divisional of application Ser. No. 08/134,098 filed Oct. 8, 1993, now U.S. Pat. No. 5,480,565.

FIELD OF THE INVENTION

This invention relates to kidney dialysis machines and, in particular, to an improved method for reprocessing the dialyzers used with such machines.

BACKGROUND OF THE INVENTION

Kidney dialysis machines have been successfully used for the past 30 years to aid patients suffering from various forms of kidney disease. The machines are used with a cartridge, known in the art as a "dialyzer" or "artificial kidney", which contains a semipermeable membrane. The membrane divides the dialyzer into a blood compartment and a dialysate compartment. In broad outline, as the patient's blood passes through the blood compartment, waste products move across the membrane into the dialysate compartment, while high molecular weight blood components are retained in the blood compartment.

The structure of a typical dialyzer 13 employing hollow fibers 11 as the semipermeable membrane is shown in FIG. 1. The blood compartment of the dialyzer comprises the space inside of fibers 11 while dialysate compartment comprises the space outside the fibers. To form these compartments, fibers 11 are embedded in potting compound 15, 17 at their ends. The patient's blood passes through the dialyzer by means of entrance port 19 and exit port 21, while dialysate enters and leaves by ports 23 and 25, respectively.

When initially introduced, dialyzers were one use devices. With time, however, efforts were made to reprocess dialyzers to reduce the overall cost to the patient and the health care delivery system. The cost benefits achieved by reprocessing are significant. For example, a new dialyzer typically costs around $30. With reprocessing, a dialyzer can be used between 5 and 20 times without substantial lost of efficacy. The cost of reprocessing is approximately $4 per unit. Accordingly, by employing reprocessing, the dialyzer cost per treatment is conservatively less than about $10, as opposed to $30 if a new dialyzer were used for each treatment.

Since a typical patient receives approximately 150 treatments per year and since in the United States alone approximately 120,000 patients are on hemodialysis, the cost savings achieved by reprocessing are enormous. For example, based on the $30 to $10 differential discussed above, the savings would amount to 360 million dollars per year if reprocessing were used for all U.S. patients. At present, approximately 75% of the treatments performed in the United States employ reprocessed dialyzers.

In overview, reprocessing of dialyzers involves three basic steps: 1) cleansing, 2) efficacy confirmation, and 3) disinfection.

The cleansing of a dialyzer involves removing residual blood and organic material from the blood side and removing dialysate from the dialysate side of the semipermeable membrane. Equipment specifically designed to perform this step is commercially available. Such equipment causes cleansing solution to pass through the walls of the hollow fibers making up the dialyzer so as to remove undesired material from both the blood and dialysate compartments. A number of cleansing solutions for use in this step are known, including solutions composed of purified water and bleach, a peracetic acid mixture, hydrogen peroxide, or other cleansing agents. Purified water by itself has also been used for cleansing.

The efficacy confirmation step involves determining 1) that the membrane and associated structural components of a cleansed dialyzer still maintain a barrier between the blood and dialysate compartments, and 2) that the cleansed dialyzer has a membrane area substantially equivalent to a new dialyzer. This step is typically performed by measuring the volume of the blood compartment.

The disinfection step involves killing microorganisms which may have contaminated the blood or dialysate compartments during or after use. Again, equipment specifically designed to perform this step is commercially available and in many cases, the same piece of equipment performs the cleansing, testing, and disinfection functions.

Of these three steps, disinfection has proven to be most difficult, both because it must be highly effective if reprocessed dialyzers are to be safe and because the critical properties of the dialyzer's semipermeable membrane must remain substantially unchanged by the disinfection process. Also, the semipermeable membranes used in dialyzers have large areas, high porosities, and, after use, are coated with proteins and other organic materials. As a result, the membrane of a used dialyzer is highly susceptible to microbial growth and effective killing of microorganisms on such a membrane, without damaging the membrane, is difficult to accomplish.

Prior to the present invention, two basic types of disinfection have been employed in the art. See Deane et al., "Multiple Use of Hemodialyzers," In: *Replacement of Renal Function by Dialysis*, 3rd edition, edited by J F Maher, Kluwer Academic Publishers, Boston, Mass., 1989, pages 400–416.

The most common approach uses a disinfecting solution containing a toxic chemical such as formaldehyde, glutaraldehyde, or a mixture of peracetic acid, hydrogen peroxide, and acetic acid. See, for example, *AAMI Recommended Practice for Reprocessing Hemodialyzers*, Association for the Advancement of Medical Instrumentation, Arlington, Va., 1993. Because of the toxicity of these disinfecting chemicals, this approach suffers from the problem of ensuring that all of the disinfecting solution is removed from the dialyzer prior to reuse. Also, disinfecting solutions based on a peracetic acid mixture raise concerns regarding the solution's efficacy in view of its limited shelf life and inactivation by organic material. Further, the use of formaldehyde raises environmental concerns in view of the known carcinogenic effects of this compound.

In connection with these prior disinfecting solutions, it should be noted that in practice, only high level disinfection and not sterilization has been achieved, that is, although the solutions have killed all pathogenic organisms, they have not made the reprocessed dialyzers free of all microbial viability. In contrast, as discussed in detail below, the present invention achieves sterilization of the dialyzer.

A second approach to disinfection involves heat treating the dialyzer at a temperature above 100° C. for approximately 20 hours. See Kaufman et al., "Clinical Experience with Heat Sterilization for Reprocessing Dialyzers," *ASAIO Transactions*, Vol. 38, No. 3, July–September 1992, pages M338–M340. Although this approach has been found to work successfully in practice and avoids the toxicity problem associated with disinfecting solutions of the type discussed above, it too suffers from problems. In particular, it can only be used with dialyzers which can withstand the high temperatures and long processing times at such temperatures required by the procedure. Also, even for dialysis membranes which can withstand these processing conditions, a high rate of failure of the structural components of the dialyzer, e.g., the potting material for the hollow fibers, has been observed. This failure rate limits the number of reuses of the dialyzer to approximately 10 times.

The use of citric acid in connection with the cleansing of dialysis machines has been disclosed in a number of patent publications. In particular, Tell et al., U.S. Pat. No. 4,690, 772, discloses a sterilant comprising sodium chlorite, citric acid, and a sodium bicarbonate buffer. Sodium chlorite is toxic and thus this sterilant falls into the chemical disinfection category discussed above.

EPO Patent Publication No. 393,386 discloses the use of a citric acid solution to clean a dialysis machine after bicarbonate dialysis, specifically, to decalcify the machine. Similarly, EPO Patent Publication No. 505,763 discloses the use of citric acid solutions to disinfect dialysis machines. In particular, this publication states that such a solution can be applied to the machine's water-circuit. A water-circuit is used in a dialysis machine to form the dialysate from a chemical concentrate. It is not part of the dialyzer.

Although these references do mention the use of citric acid in connection with dialysis machines, none of them discloses or suggests that citric acid can be used to disinfect a dialyzer. As discussed in detail below, in accordance with the invention, it has been surprisingly found that dialyzers not only can be disinfected but can be sterilized at temperatures below 100° C. by means of a citric acid solution provided that the dialyzer's semipermeable membrane is exposed to the citric acid solution for a sufficient period of time, i.e., at least about 15 hours. Such exposure has been found to leave both the permeability of the membrane and the integrity of the dialyzer essentially unchanged.

SUMMARY OF THE INVENTION

In view of the foregoing state of the art, it is an object of this invention to provide an improved method for reprocessing dialyzers. It is a particular object of the invention to provide a method for reprocessing dialyzers which does not employ toxic chemicals. It is a further object of the invention to provide a method for reprocessing dialyzers which minimizes the possibility of damage to the dialyzer's semipermeable membrane or structural components. It is an additional object of the invention to provide an improved method for storing dialyzers prior to use.

To achieve these and other objects, the invention in accordance with certain of its aspects provides a method for reprocessing a dialyzer comprising the steps of:

(a) filling the blood and dialysate compartments of the dialyzer with an aqueous solution which comprises citric acid at a concentration of between about 1.0 and about 5.0 weight percent per volume; and (b) subjecting the dialyzer containing the aqueous solution to an elevated temperature less than 100° C. for a period of time sufficient to kill pathogenic organisms and viruses contained within the dialyzer.

In certain preferred embodiments of the invention, step (b) is performed for between about 15 hours and about 25 hours at a temperature greater than about 90° C., e.g., for about 20 hours at a temperature of about 95° C. The preferred concentration of citric acid in the aqueous solution for these times and temperatures is about 1.5 weight percent by volume. More generally, it is preferred to perform step (b) for a period of time and at a temperature and citric acid concentration which will achieve sterilization of the dialyzer, i.e., in addition to killing pathogenic organisms and viruses, bacterial spores are also killed.

The citric acid used in the practice of the invention will normally be in its monohydrate form, i.e., it will have the formula $HOOCCH_2C(OH)(COOH)CH_2COOH.H_2O$. A weight percent by volume (hereinafter abbreviated as "wt. %") of, for example, 1.5 means that 15.0 grams of monohydrate citric acid are contained in 1.0 liter of solution.

In accordance with other aspects of the invention, the blood and dialysate compartments of a dialyzer are filled with an aqueous citric acid solution having a concentration in the range of 1.0 wt. % to 5.0 wt. % during storage. Such a solution serves as a bacteriostatic agent and thus combats accidental contamination of the dialyzer prior to use.

In accordance with further aspects of the invention, citric acid reprocessing and citric acid storage are employed as process steps in an overall hemodialysis procedure.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

DESCRIPTION OF THE PREFERRED EMBODIMENTS

As discussed above, the present invention relates to the reprocessing of a dialyzer using a combination of citric acid at a concentration in the 1.0–5.0 wt. % range, a temperature in the 90°–100° C. range, and a processing time in the 15–25 hour range.

Figure 1:
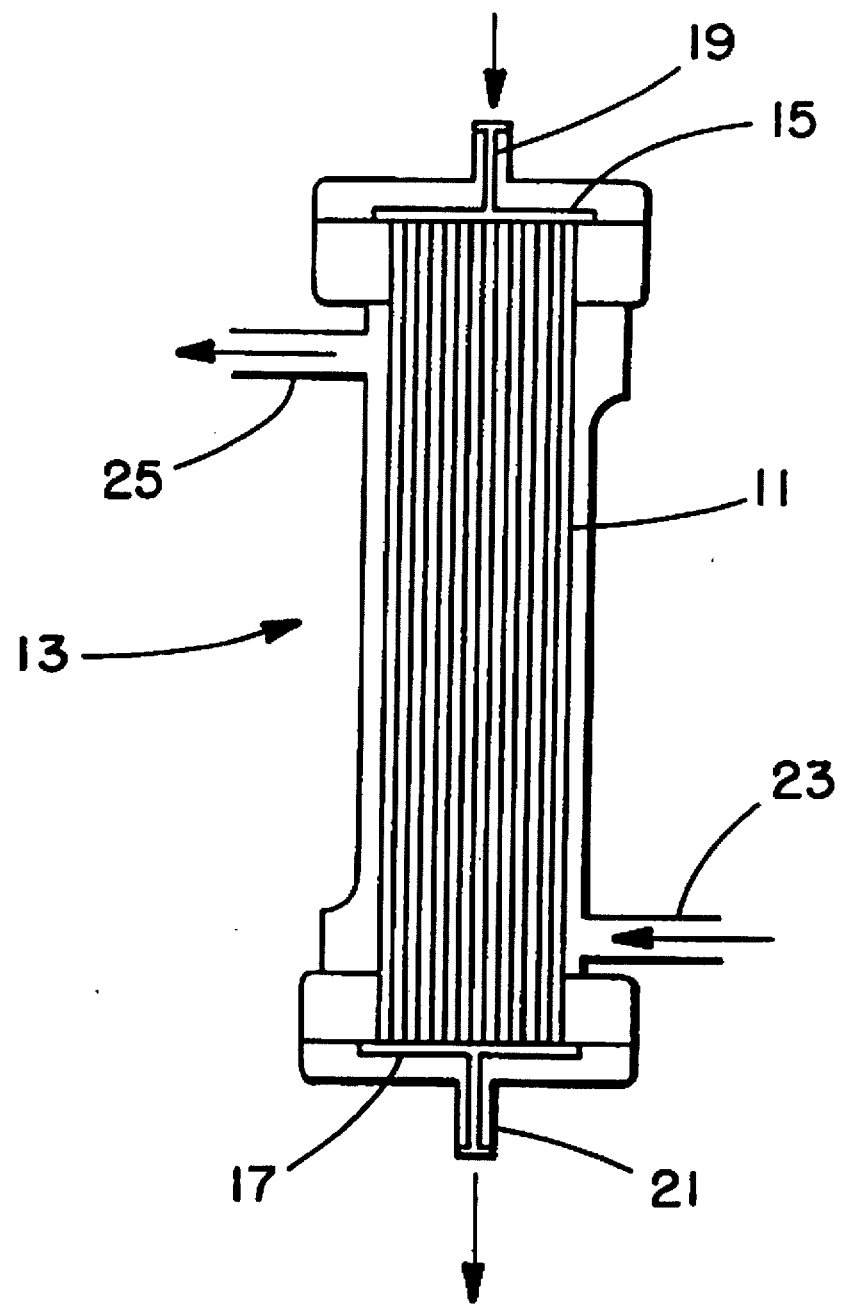
FIG. 1 is a schematic drawing showing the construction of a hollow fiber dialyzer.

The invention can be used with a variety of dialyzers now known or subsequently developed. In particular, it can be used with hollow fiber dialyzers of the type illustrated in FIG. 1 and with plate type dialyzers in which the semipermeable membrane is in the form of pairs of sheets or plates which separate the blood and the dialysate.

In general terms, citric acid concentrations in the 1.0–5.0 wt. % range will cause essentially no damage to the materials conventionally used in the manufacture of dialyzers. Incubation at 90°–100° C. for 15–25 hours, however, may cause some degradation of some dialyzer materials. Accordingly, preliminary studies should be performed to confirm that structural and functional characteristics of a particular dialyzer will not be substantially compromised by the process of the invention.

The citric acid solutions used in the practice of the invention preferably comprise drug grade citric acid and ultrapure water, i.e., water which has been treated to remove all minerals by reverse osmosis and which has then been passed through a microbial and pyrogen filter. Preferably, the citric acid solution contains only water and citric acid, although if desired other non-toxic chemicals can be included in the solution.

The overall process of the invention follows the three basic reprocessing steps discussed above. Thus, a used dialyzer is cleansed and tested for efficacy using commercially available reprocessing equipment. The cleansing is preferably performed using purified water without any added cleansing agents so as to avoid the introduction of toxic chemicals which would later have to be removed. If desired, a cleansing solution containing citric acid, which is non-toxic, can be used.

After efficacy confirmation, the dialysate and blood compartments of the used dialyzer are filled with the 1.0–5.0 wt. % citric acid solution, again using commercially available reprocessing equipment. The inlet and outlet ports of the dialyzer are sealed and a heat sensitive tape is preferably affixed to the dialyzer to serve as an indicator that the heating step of the process has been performed. The dialyzer is then preferably placed in a heat resistant plastic bag and a second heat sensitive tape is applied to the outside of the bag to serve as a further indicator that the heating step has been performed.

The heating itself can be performed using a conventional convection oven or other heating device. Preferably, a continuous recording is made of the temperatures to which the dialyzer has been exposed. As discussed above, the dialyzer needs to be exposed to an elevated temperature for a period of time sufficiently long to at least kill pathogenic organisms and viruses. Preferably, the dialyzer is sterilized by the heating step. Such sterilization can, for example, be achieved by using a temperature of at least 95° C. and a heating period of at least 15 hours. To minimize damage to the structure and materials of the dialyzer, the temperatures to which the dialyzer is exposed are kept below 100° C.

It should be noted that the internal temperature of a dialyzer rises relatively slowly when placed in a heated environment. For example, using thermocouples, it has been established that a period of 3–4 hours is required for the core temperature of a dialyzer to reach equilibrium with its surrounding temperature. The heating step thus must be sufficiently long to accommodate this initial period during which the core of the dialyzer is below the target temperature. Also, when multiple dialyzers are processed, the individual dialyzers should be placed in the heating device and spaced from one another so that all of the dialyzers will undergo a similar course of heating.

After the heat treatment step, the reprocessed dialyzers are ready for use in a conventional kidney dialysis treatment. As is standard, reprocessed dialyzers are not transferred from one patient to another.

Prior to use, the citric acid solutions are removed from the blood and dialysate compartments and the dialyzer is pressure tested to confirm its integrity. The blood compartment of the dialyzer is then primed with sterile saline and the saline recirculated through the blood compartment while dialysate is passed through the dialysate compartment until both the dialysate and blood compartments are free of air. This priming and recirculation procedure has been found to rapidly remove all residual traces of citric acid as evidenced by the fact that the pH of the solution in the blood compartment increases to that of the dialysate within a few minutes. Since citric acid is non-toxic and indeed is a normal constituent of food, an analysis of the saline priming solution in the blood compartment does not have to be routinely performed prior to the dialysis treatment. In comparison, when a toxic disinfectant is used, such a test is required prior to initiating dialysis.

Dialysis patients typically undergo dialysis treatments three times a week, e.g., on Mondays, Wednesdays, and Fridays. The reprocessing procedures of the invention are readily employed in this schedule. After a dialysis treatment, the used dialyzer can be held at room temperature for a short period of time or in a refrigerator for a somewhat longer period of time until reprocessing begins. Preferably, reprocessing is begun within about 2 hours of the end of the dialysis treatment. As discussed above, the heating step typically is performed for about 20 hours. Thereafter, the dialyzer is preferably stored with the citric acid solution still in the blood and dialysate compartments where it acts as a bacteriostatic agent. For the typical three-time-a-week dialysis schedule, this storage period will be approximately 24 hours, except on weekends when it will be approximately 48 hours. After the storage period, the reprocessed dialyzer is used as described above and the process is thereafter repeated multiple times until the dialyzer fails either the pre-heating efficacy confirmation test or the post-heating integrity test.

Without intending to limit it in any manner, the present invention will be more fully described by the following examples.

EXAMPLE 1

This example demonstrates the ability of the process of the invention to sterilize dialyzers.

The dialyzers used in these experiments were manufactured by Fresenius AG, Oberursel, Germany, and sold under the designation Hemoflow F80. The tests were performed using spores of *Bacillus Stearothermophilus*.

A 1.5 wt. % citric acid solution was prepared using citric acid monohydrate obtained from J. T. Baker (A.C.S. grade, 99.5% pure). The citric acid was dissolved w/v in deionized water to a concentration of 1.5 wt. %, i.e., 45.007 gms of the monohydrate were dissolved in 3.0 liters of water.

*B. Stearothermophilus* GBL 1045 (ATCC 7953) was grown on the surface of trypticase soy agar (TSA) plates for 10 days at 54° to 56° C. Spores were harvested by flooding the surface with sterile deionized water. The suspension was centrifuged at approximately 1000 rpm and washed three times with sterile deionized water. The suspension was sonicated for 15 minutes and then heat shocked at 80° C. for 20 minutes. The count was determined to be $2.1 \times 10^6$ spores/ml by plate count.

The Fresenius Hemoflow F80 dialyzers were prewarmed in an oven (Baxter) for two hours at 95° C., and three liters of 1.5 wt. % citric acid solution and two liters of sterile deionized water were preincubated overnight in a 95° C. water bath so as to equilibrate to the oven temperature of 95° C. Immediately upon removal from equilibration, the citric acid and the deionized water solutions were inoculated with an aqueous suspension of spores of *B. stearothermophilus* to yield a final concentration of approximately $10^4$ spores/ml.

For each incubation period tested, two dialyzers were filled with 200 ml of the prewarmed citric acid spore suspension and one dialyzer was filled with 200 ml of the prewarmed water spore suspension. The dialyzers were sealed and returned to the 95° C. oven for heating.

Experiments were performed for seven time periods, i.e., 0 minutes, 30 minutes, 1 hour, 2 hours, 4 hours, 6 hours, and 24 hours. At each of these times, inoculated dialyzers were removed for bacterial counts. In particular, the entire contents of each dialyzer was removed and ten-fold serial dilutions were made in sterile saline and decimal portions ($10^{-1}$, $10^{-2}$, $10^{-3}$) were filtered through 0.45μ membrane filters. The filters were then successively washed three times with 100 ml sterile saline and planted on TSA plates which were then incubated for 48 hours at 54° to 56° C.

In addition to the above dilutions, 1.0 ml and 10 ml portions of the dialyzer contents were filtered through sterile 0.45μ membrane filters. The filters were washed and cultured as above. The remaining approximately 188 ml of spore suspension in each dialyzer was also filtered through 0.45μ membrane filters at certain time points so as to recover low numbers of survivors that might not be recovered by use of the low volume dilution steps. To be sure that all of the spores were eluted from the dialyzers (especially at the longer contact times), the dialyzers (previously emptied) were flushed with approximately 200 ml of sterile deionized water to assure that all of the spores were removed from the internal parts of the dialyzer. The flushed suspensions were membrane filtered and cultured on TSA as above.

All plates were enumerated by gross observation under magnification with a Quebec colony counter.

Figure 2:
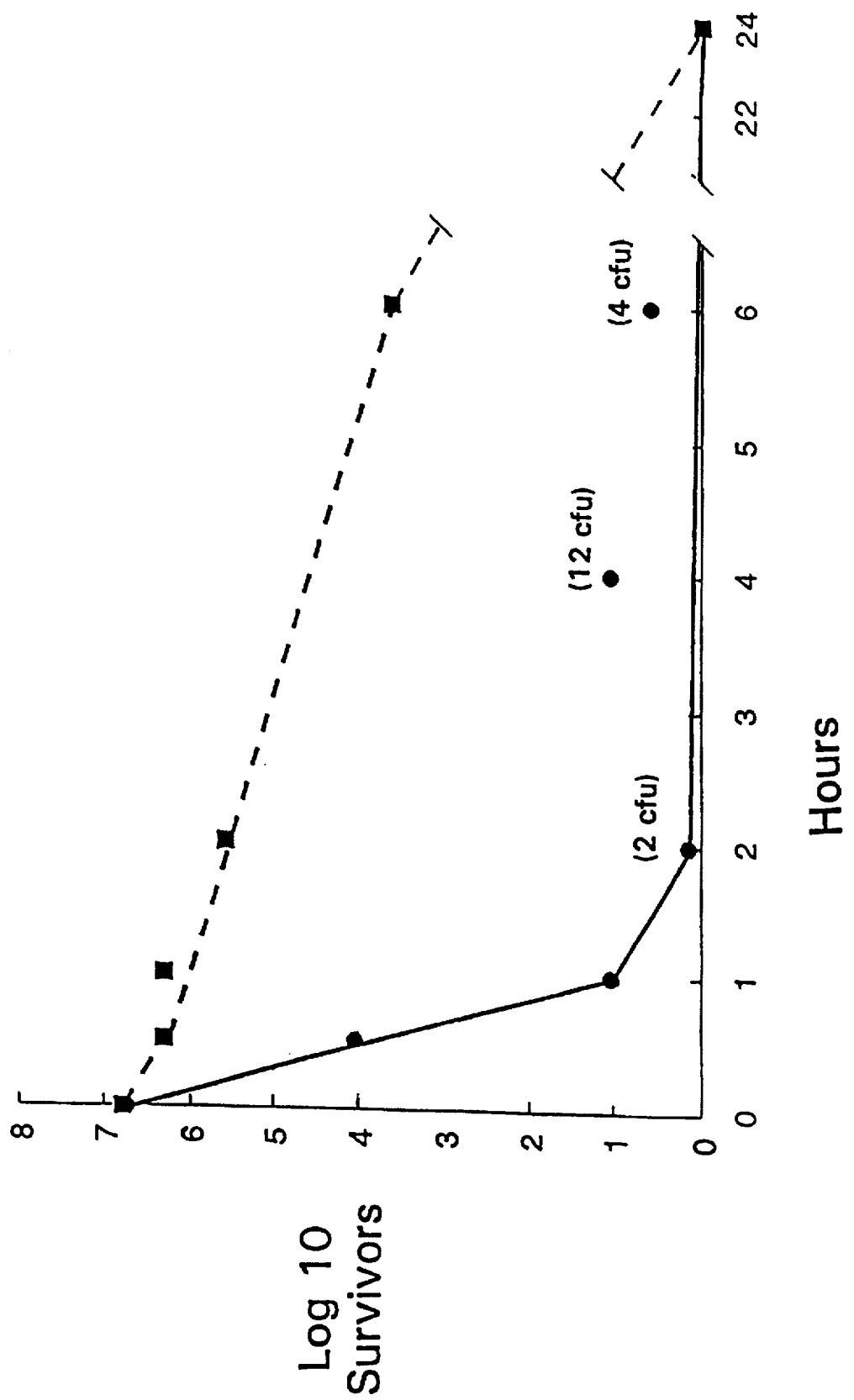
FIG. 2 is a plot of surviving spores per dialyzer versus time for dialyzers inoculated with spores of *Bacillus stearothermophilus* as described in Example 1. The data for dialyzers containing a 1.5 wt. % citric acid solution is shown by circles and that for a control consisting of purified water without citric acid is shown by squares. The data point at 24 hours comprises both a circle and a square. Both the experimental and control dialyzers were incubated with the spore solution at 95° C. for the indicated times. The cfu values which appear next to the circle data points represent the average number of colony forming units per dialyzer at the indicated times.

The results of these experiments are summarized in Table 1 and FIG. 2. As shown in Table 1, the citric acid solution was approximately seven times more efficient in killing the *B. stearothermophilus* spores than water alone ($D_{water}/D_{citric\ acid}=96/13.2=7.3$).

As shown in FIG. 2, at 6 hours, the average number of colony forming units (cfu) in the citric acid solutions removed from the dialyzers was 4 while at 24 hours, the cfu count had been decreased to less than 1. For comparison, the controls containing only water had significantly higher cfu counts at 6 hours and at all earlier times.

These data show that sterilization of the dialyzers was achieved in about 15 hours using the 1.5 wt. % citric acid solution and heating to 95° C.

In a separate set of experiments, a 1.5 wt. % citric acid solution was tested for its ability to kill test cultures of the following microorganisms at 95° C.: *Staphylococcus aureus, Escherichia coli, Pseudomonas aeruginosa, Candida albicans, Aspergillus niger, Pseudomonas maltophilia,* and *Mycobacterium Chelonae. Pseudomonas maltophilia, Staphylococcus aureus,* and *Escherichia coli* are representative of the microorganisms most likely to infect a used dialyzer. *Pseudomonas aeruginosa, Candida albicans, Aspergillus niger,* and *Mycobacterium chelonae* can also infect a used dialyzer, but the probability of such an infection is significantly smaller. For each of these seven types of microorganisms a rapid kill was achieved, i.e., in less than about 30 minutes. These experiments show that disinfection with a 1.5 wt. % citric acid solution at 95° C. can be readily achieved.

EXAMPLE 2

This example demonstrates that at room temperature, a 1.5 wt. % citric acid solution will kill vegetative microorganisms of the type most likely to be accidentally introduced into a reprocessed dialyzer. Accordingly, such a solution will maintain the sterility of a reprocessed dialyzer with regard to such microorganisms during storage at room temperature, that is, the citric acid solution will serve as a bacteriostatic agent at room temperature for the reprocessed dialyzer. It should be noted that baring a break in the integrity of the reprocessed dialyzer, the dialyzer will remain sterile during storage. Accordingly, the citric acid solution provides backup protection for sterility, rather than being the primary source of sterility.

A 1.5 wt. % citric acid solution was tested for its ability to kill test cultures of the following microorganisms at room temperature: *Staphylococcus aureus, Escherichia coli, Pseudomonas aeruginosa, Candida albicans, Aspergillus niger, Pseudomonas maltophilia,* and *Mycobacterium chelonae.*

*Staphylococcus aureus, Escherichia coli, Pseudomonas aeruginosa* were each reduced in number by more than four logs in less than 3 hours. *Pseudomonas maltophilia* were reduced in number by more than five logs in less than about 6 hours. As discussed above, *Pseudomonas maltophilia, Staphylococcus aureus,* and *Escherichia coli* are the microorganisms most likely to available for infection of a reprocessed dialyzers.

*Candida albicans, Aspergillus niger,* and *Mycobacterium chelonae* were not killed by the 1.5 wt. % citric acid solution at room temperature. However, as discussed above, the probability of an infection of a reused dialyzer with these microorganisms is even less than that with one of the microorganisms which were killed.

EXAMPLE 3

This example demonstrates that dialyzers reprocessed with citric acid in accordance with the invention are effective in performing hemodialysis on patients with renal failure.

Hemodialysis was performed on a series of patients using Fresenius Hemoflow F80 dialyzers reprocessed in accordance with the invention, specifically, the dialyzers were reprocessed at 95° C. for 20 hours using a 1.5 wt. % citric acid solution following the procedures described above in connection with the preferred embodiments. No damage to the dialyzers' potting compound or casing was observed after five reprocessings. For comparison, heat sterilization using purified water and a temperature above 100° C., i.e., 105° C., resulted in visible structural damage at as low as one to three reprocessings.

Clearance data for small molecules was measured for a reprocessed dialyzer during dialysis of a patient and was found to be substantially the same as the clearance achieved by the same dialyzer before its first use. Predialysis pyrogen analyses and cultures were performed for all reprocessed dialyzers used in the study and were found to be negative. Hydraulic and protein permeabilities, specifically, permeability for albumin, were measured for all reprocessed dialyzers and were found to be substantially the same as the values for a new dialyzer. Although the sample was small (i.e., four patients, 3–5 reprocessings per patient) and thus statistical analysis of the data cannot be performed, no morbidity or mortality occurred.

EXAMPLE 4

This example illustrates that the combination of citric acid and heating at 95° C. for 20 hours does not substantially change the permeability or clearance of small molecules by a hollow fiber dialyzer.

New Fresenius Hemoflow F80 dialyzers were subjected to the process of the invention, specifically, the dialyzers were subjected to heating at 90° C. for 20 hours using a 1.75 wt.

% citric acid solution following the procedures described above in connection with the preferred embodiments. Seven dialyzers were used in this study with five of the dialyzers being reprocessed twelve times and two being reprocessed five times.

No significant change in clearance, hydraulic permeability, or permeability to protein, specifically, albumin, was seen for any of the dialyzers.

COMPARATIVE EXAMPLE

This example illustrates the difficulty in predicting the effects of a reprocessing procedure on the structure and performance of a dialyzer.

New Fresenius Hemoflow F80 dialyzers were filled with a 0.6% sodium hypochlorite solution ($NaOCl.5H_2O$), rinsed and then filled with purified water. Thereafter, the dialyzers were heated at 95° C. for 20 hours.

The dialyzers were then tested for clearance of small molecules, hydraulic permeability, and permeability to protein, specifically, albumin. Clearance for the dialyzers was within the normal range. However, both the hydraulic permeability and the permeability to protein were significantly increased to the point where the reprocessed dialyzers were unsuitable for reuse.

In comparison, as the data of Examples 2–4 show, the process of the present invention does not adversely change the permeability characteristics of the dialyzer. In this regard, it should be noted that in the process of the invention, the citric acid solution remains in the dialyzer throughout the heating step, while in the sodium hypochlorite experiment, the disinfecting solution was replaced with water prior to heating. This illustrates the surprising gentleness of the process of the invention to the dialyzer while still being completely effective in achieving sterilization.

Although preferred and other embodiments of the invention have been described herein, other embodiments may be perceived by those skilled in the art without departing from the scope of the invention as defined by the following claims.

TABLE 1

| | D Values* | |
|---|---|---|
| Time (hours) | Dialyzers With 1.5 wt. % Citric Acid at 95° C. (minutes) | Dialyzers With Purified Water at 95° C. (minutes) |
| 0.5 | 11.0 | 62.5 |
| 1.0 | 10.5 | 125.0 |
| 2.0 | 18.2 | 100.0 |
| Average | 13.2 | 96.0 |

*$D = T/(\log_{10} N_0 - \log_{10} N_T)$, where $N_0$ is the initial cfu value and $N_T$ is the cfu value at the end of incubation time T.

What is claimed is:

1. A dialyzer comprising a semipermeable membrane which divides the dialyzer into a blood compartment and a dialysate compartment, each of said compartments containing an aqueous solution of citric acid at a concentration sufficient for the solution to be bacteriostatic at room temperature, said aqueous solution being free of toxic chemicals and said dialyzer when filled with said aqueous solution having been exposed only to temperatures below 100° C.

2. The dialyzer of claim 1 wherein the concentration of citric acid is between about 1.0 weight percent by volume and about 5.0 weight percent by volume.

3. The dialyzer of claim 1 wherein the concentration of citric acid is about 1.5 weight percent by volume.

4. The dialyzer of claim 1 wherein citric acid is the only active ingredient in the aqueous solution.

* * * * *